United States Patent
Sato

(10) Patent No.: US 10,016,670 B2
(45) Date of Patent: Jul. 10, 2018

(54) MOTION ANALYSIS METHOD AND MOTION ANALYSIS DEVICE

(71) Applicant: SEIKO EPSON CORPORATION, Tokyo (JP)

(72) Inventor: Masafumi Sato, Hara-mura (JP)

(73) Assignee: SEIKO EPSON CORPORATION, Tokyo (JP)

(*) Notice: Subject to any disclaimer, the term of this patent is extended or adjusted under 35 U.S.C. 154(b) by 6 days.

(21) Appl. No.: 14/666,068

(22) Filed: Mar. 23, 2015

(65) Prior Publication Data

US 2015/0196823 A1 Jul. 16, 2015

Related U.S. Application Data

(62) Division of application No. 14/306,611, filed on Jun. 17, 2014.

(30) Foreign Application Priority Data

Jun. 21, 2013 (JP) ................... 2013-130652

(51) Int. Cl.
*G01P 15/00* (2006.01)
*A63B 71/06* (2006.01)
(Continued)

(52) U.S. Cl.
CPC ........ *A63B 71/0619* (2013.01); *A61B 5/1122* (2013.01); *A61B 5/6895* (2013.01); *A63B 24/0003* (2013.01); *A63B 69/36* (2013.01); *A63B 69/3608* (2013.01); *G01P 15/02* (2013.01); *G09B 19/003* (2013.01); *A61B 5/744* (2013.01); *A61B 2562/0219* (2013.01); *A63B 24/0006* (2013.01); *A63B 2071/0647* (2013.01); *A63B 2208/0204* (2013.01); *A63B 2220/18* (2013.01); *A63B 2220/40* (2013.01); *A63B 2220/51* (2013.01); *A63B 2220/803* (2013.01);
(Continued)

(58) Field of Classification Search
None
See application file for complete search history.

(56) References Cited

U.S. PATENT DOCUMENTS 4,270,753 A * 6/1981 Maroth ................. G01P 15/032
473/233
7,264,554 B2 9/2007 Bentley
(Continued)

FOREIGN PATENT DOCUMENTS

JP 2008-023036 A 2/2008
JP 2008-073210 A 4/2008
(Continued)

OTHER PUBLICATIONS

Apr. 21, 2017 Office Action issued in U.S. Appl. No. 14/306,611.
Nov. 8, 2017 Office Action issued in U.S. Appl. No. 14/306,611.
Mar. 29, 2018 Office Action issued in U.S. Appl. No. 14/306,611.

*Primary Examiner* — Aditya Bhat
(74) *Attorney, Agent, or Firm* — Oliff PLC

(57) ABSTRACT

A motion analysis device includes a calculation unit which specifies a first imaginary plane, that is, a shaft plane formed by a first line segment representing a direction in which a shaft part of a sporting gear in a static posture extends and a second line segment representing a ball hitting direction, with the use of an output from an inertial sensor.

18 Claims, 13 Drawing Sheets

(51) Int. Cl.
*A63B 69/36* (2006.01)
*G01P 15/02* (2013.01)
*G09B 19/00* (2006.01)
*A61B 5/00* (2006.01)
*A61B 5/11* (2006.01)
*A63B 24/00* (2006.01)

(52) U.S. Cl.
CPC ... *A63B 2220/833* (2013.01); *A63B 2220/836* (2013.01)

(56) References Cited

U.S. PATENT DOCUMENTS

| | | | |
|---|---|---|---|
| 7,587,065 B2 | 9/2009 | Matsumoto et al. | |
| 8,523,696 B2 | 9/2013 | Kamino et al. | |
| 8,672,779 B1 * | 3/2014 | Sakyo | A63B 24/0006 473/223 |
| 9,211,439 B1 * | 12/2015 | Pedenko | A63B 24/0006 |
| 2006/0084516 A1 * | 4/2006 | Eyestone | A63B 69/3632 473/219 |
| 2006/0166737 A1 * | 7/2006 | Bentley | A61B 5/1122 463/30 |
| 2013/0005496 A1 | 1/2013 | Priester et al. | |
| 2014/0379293 A1 | 12/2014 | Sato | |
| 2015/0196823 A1 | 7/2015 | Sato | |
| 2016/0271481 A1 | 9/2016 | Sato | |

FOREIGN PATENT DOCUMENTS

| | | |
|---|---|---|
| JP | 2008-528195 A | 7/2008 |
| JP | 2009-020897 A | 1/2009 |
| JP | 2010-082430 A | 4/2010 |
| JP | 2011-000210 A | 1/2011 |
| JP | 2011-103925 A | 6/2011 |
| JP | 2013-009917 A | 1/2013 |
| JP | 2015-002910 A | 1/2015 |

* cited by examiner

MOTION ANALYSIS METHOD AND MOTION ANALYSIS DEVICE

This is a Divisional application of application Ser. No. 14/306,611 filed Jun. 17, 2014 which claims priority to JP2013-130652 filed Jun. 21, 2013. The disclosure of the prior applications is hereby incorporate by reference herein in their entirety.

BACKGROUND

1. Technical Field

The present invention relates to a motion analysis method and a motion analysis device.

2. Related Art

For example, in golf, which is a specific example of sports, the concept of the swing plane is commonly known. The swing plane is equivalent to the trajectory of the golf club when swung. For example, according to JP-A-2009-20897 and JP-A-2008-23036, a golf swing made by a subject is shot with a camera from behind the subject and the swing plane is specified based on the shot image.

The technique for finding the swing plane according to JP-A-2009-20897 is to find at least two specific points in the swing from image data and analyze the swing plane based on the two points. In this technique, first, after the swing is finished, it is necessary to edit the image data and carry out work to find specific points. Therefore, there is a problem that a large discrepancy from the actual swing plane is generated and also a problem that it is time-consuming to display the swing plane. The technique of JP-A-2008-23036, too, requires some work to edit image data and therefore has similar problems to those of JP-A-2009-20897.

In golf swing coaching, indicators such as shaft plane and Hogan plane are known. The shaft plane is a plane formed by the direction of the longitudinal axis of the shaft of the golf club when the golfer is at address position (static state) and a target line (ball hitting direction). The Hogan plane is a plane formed by an imaginary line connecting the neck bottom (bottom of the neck) of the golfer and the ball when the golfer is at address position and a target line (ball hitting direction). An area between the shaft plane and the Hogan plane is called V-zone. The V-zone is defined when the golfer is at address position, and whether the ball hitting is good or not is evaluated, based on whether the golf club is in the V-zone at impact or not. If the shaft plane and the Hogan plane are shown as indicators on an image, the golfer can easily grasp points of improvement in the swing form. However, in the techniques of JP-A-2009-20897 and JP-A-2008-23036, in order to find the Hogan plane, it is necessary to shoot the form of the golfer from behind and manually draw lines with a ruler or the like, based on the shot image. Therefore, there are no previous measures to present the shaft plane and the Hogan plane easily and accurately to the golfer in golf swing analysis.

SUMMARY

An advantage of some aspect of the invention is that a motion analysis method and a motion analysis device are provided which are capable of presenting a clear indicator in analyzing the motion of a swing.

(1) According to an aspect of the invention, with the use of an output from a first inertial sensor installed above a sporting gear, calculation is carried out to specify a first imaginary plane formed by a first line segment representing a direction in which a shaft part of the sporting gear in a static posture extends and a second line segment representing a ball hitting direction.

To establish the static posture of the sporting gear, the subject reproduces the posture at the moment of impact. As a result, the posture at the moment of impact is extracted from a series of movements called "swing". The inertial sensor outputs a detection signal according to the posture of the sporting gear. The first imaginary plane is specified according to the detection signal. The first imaginary plane can depict an imaginary trajectory of the sporting gear swung in the swing. The trajectory of the sporting gear in the swing is observed in comparison with the imaginary trajectory. The movement of the subject is analyzed, based on the trajectory of the sporting gear. Thus, a clear indicator is provided with respect to the motion "swing". According to this configuration, in the case of a golf swing, the first imaginary plane can be regarded as the shaft plane, and for example, based on the inclination of the shaft plane when the subject is at address position, the subject can grasp the difference in the distance between the subject and the ball and the difference in the posture of the subject and can thoroughly examine the causes of good or bad ball hitting.

(2) The output from the first inertial sensor may include an output from an acceleration sensor. The first line segment may be decided by calculating an inclination of the shaft part of the sporting gear with respect to a direction of gravity, with the use of the output from the acceleration sensor in the static posture, and then using the inclination and length information of the shaft part.

According to this configuration, an acceleration sensor is used as the inertial sensor. Based on the output from the acceleration sensor in the static posture, for example, how much the shaft of the golf club is inclined with respect to the direction of gravity can be found. Using the inclination information and the length information of the shaft, the shaft plane can be easily specified.

(3) The second line segment may be a direction intersecting with a ball hitting surface of the sporting gear. According to this configuration, the ball hitting direction is regarded as the target line, and for example, in the case of golf, the shaft plane as the first imaginary plane is calculated. Thus, the subject can carry out a series of movements called "swing", based on an imaginary trajectory in his/her mind. Thus, good improvement can be added to the movements of the swing.

(4) According to another aspect of the invention, with the use of an output from a second inertial sensor installed above a subject's arm, a position of the subject's shoulder in a static posture is specified, and calculation is carried out to specify a second imaginary plane formed by a first line segment connecting the position of the shoulder and a ball hitting position and a second line segment representing a ball hitting direction.

According to this configuration, the second imaginary plane can be regarded as the Hogan plane, and for example, based on the inclination of the Hogan plane when the subject is at address position, the subject can grasp the difference in the distance between the subject and the ball and the difference in the posture of the subject and can thoroughly examine the causes of good or bad ball hitting.

(5) The output from the inertial sensor may include an output from an acceleration sensor. An inclination of a direction in which the subject's arm extends with respect to a direction of gravity may be calculated using the output from the acceleration sensor in the static posture, and the position of the shoulder may be decided using the inclination and length information of the subject's arm.

According to this configuration, an acceleration sensor is used as the inertial sensor. Based on the output from the acceleration sensor in the static posture, for example, how much the direction in which the subject's arm extends is inclined with respect to the direction of gravity can be found. Using the inclination information and the length information of the arm, the position of the subject's shoulder can be specified and the Hogan plane can be easily specified.

(6) The second line segment may be a direction intersecting with a ball hitting surface of the sporting gear. According to this configuration, the ball hitting direction is regarded as the target line, and for example, in the case of golf, the Hogan plane as the second imaginary plane is calculated. Thus, the subject can carry out a series of movements called "swing", based on an imaginary trajectory in his/her mind. Therefore, good improvement can be added to the movements of the swing.

(7) According to still another aspect of the invention, a motion analysis method includes: calculating, with the use of an output from a first inertial sensor mounted above a sporting gear, to specify a first imaginary plane formed by a first line segment representing a direction in which a shaft part of the sporting gear in a static posture extends and a second line segment representing a ball hitting direction; and specifying, with the use of an output from a second inertial sensor installed above a subject's arm, a position of the subject's shoulder in the static posture, and calculating to specify a second imaginary plane formed by a third line segment connecting the position of the shoulder and a ball hitting position and the second line segment representing the ball hitting direction.

According to this configuration, for example, in the case of a golf swing, the first imaginary plane can be regarded as the shaft plane, and the second imaginary plane can be regarded as the Hogan plane. Then, for example, based on the inclination of the Hogan plane when the subject is at address position, the subject can grasp the difference in the distance between the subject and the ball and the difference in the posture of the subject and can thoroughly examine the causes of good or bad ball hitting.

(8) The first imaginary plane may be rotated about the second line segment as a rotation axis, to specify a second imaginary plane. According to this configuration, for example, in the case of golf, if an inertial sensor is installed only on the shaft of the golf club, both the shaft plane as the first imaginary plane and the Hogan plane as the second imaginary plane can be specified.

(9) The first imaginary plane and the second imaginary plane may be displayed. To the subject, the imaginary planes are presented visually in a three-dimensional space. In response to the presentation of the imaginary planes, the subject can clearly imagine an imaginary trajectory of the sporting gear. Based on the imaginary trajectory in his/her mind, the subject can carry out a series of movements called "swing". Thus, good improvement can be added to the movement of the swing.

(10) A trajectory of a swing may be displayed, superimposed on the first imaginary plane and the second imaginary plane. To the subject, an area (V-zone) between the first imaginary plane and the second imaginary plane and the trajectory of the sporting gear can be simultaneously displayed in a three-dimensional space. The subject can visually compare his/her own swing with the imaginary planes. For example, if change and observation of the form is repeated, good improvement can be added to the form of the golf swing through trial and error.

(11) According to yet another aspect of the invention, a motion analysis device includes: a first calculation unit which specifies, with the use of an output from a first inertial sensor mounted above a sporting gear, a first imaginary plane formed by a first line segment representing a direction in which a shaft part of the sporting gear in a static posture extends and a second line segment representing a ball hitting direction; and a second calculation unit which specifies, with the use of an output from a second inertial sensor installed above a subject's arm, a position of the subject's shoulder in the static posture, and specifies a second imaginary plane formed by a third line segment connecting the position of the shoulder and a ball hitting position and the second line segment representing the ball hitting direction.

To establish the static posture of the sporting gear, the subject reproduces the posture at the moment of impact. As a result, the posture at the moment of impact is extracted from a series of movements called "swing". The inertial sensors output a detection signal according to the posture of the sporting gear. The imaginary planes are specified according to the detection signal. The imaginary planes can depict an imaginary trajectory of the sporting gear swung in the swing. The trajectory of the sporting gear in the swing is observed in comparison with the imaginary trajectory. The movement of the subject is analyzed, based on the trajectory of the sporting gear. Thus, a clear indicator is provided with respect to the motion "swing".

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, an embodiment of the invention will be described with reference to the accompanying drawings. The following embodiment should not unduly limit the content of the invention described in the appended claims. Not all the configurations described in this embodiment are necessarily essential as elements of the invention.

1. Configuration of Golf Swing Analysis Device According to First Embodiment

Figure 1:
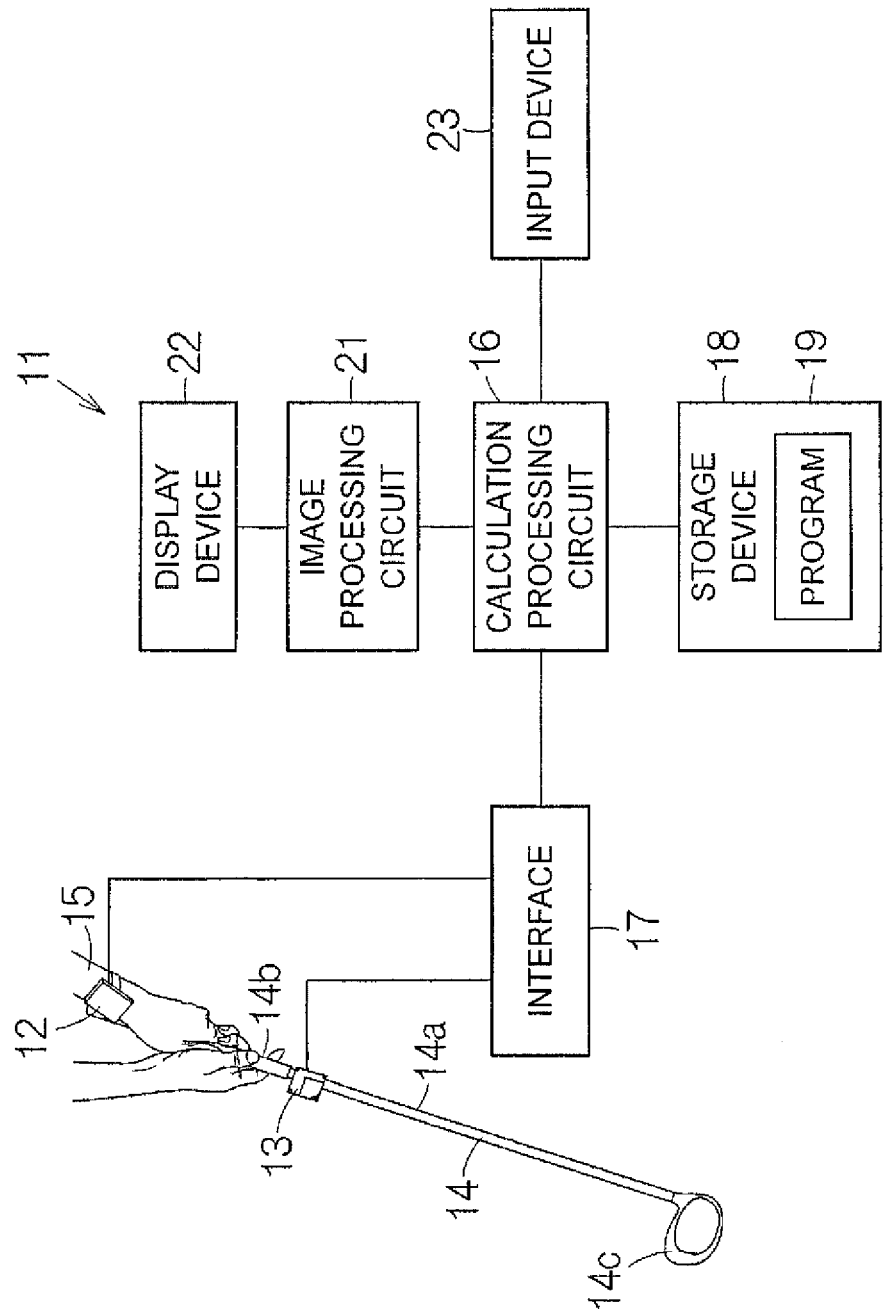
FIG. 1 is a conceptual view schematically showing the configuration of a golf swing analysis device according to a first embodiment of the invention.

FIG. 1 schematically shows the configuration of a golf swing analysis device (motion analysis device) 11 according to a first embodiment of the invention. The golf swing analysis device 11 has, for example, a first inertial sensor 12 and a second inertial sensor 13. An acceleration sensor and a gyro sensor are incorporated in the first and second inertial sensors 12, 13. The acceleration sensor can detect each one of accelerations generated in three axial directions that are orthogonal to each other. The gyro sensor can detect each one of angular velocities about each of the three orthogonal axes. The first and second inertial sensors 12, 13 output a detection signal. Based on the detection signal, the acceleration and angular velocity are specified for each axis. The acceleration sensor and the gyro sensor detect information of acceleration and angular velocity. The first inertial sensor 12 is mounted on a golfer's upper limb (for example, on the golfer's left arm if the golfer is right-handed) 15. While an example in which the first inertial sensor 12 is mounted on the golfer's forearm is given here, the first inertial sensor 12 may also be mounted at a part of the golfer's upper body such as upper arm or both shoulders. The second inertial sensor 13 is mounted on a golf club (sporting gear) 14. The golf club 14 has a shaft 14a and a grip 14b. The grip 14b is held by the hands. The grip 14b is formed coaxially with the longitudinal axis of the shaft 14a. A club head 14c is connected to a distal end of the shaft 14a. Preferably, the second inertial sensor 13 is mounted on the shaft 14a or the grip 14b as a shaft part of the golf club 14. The first and second inertial sensors 12, 13 may be fixed in such a way that the first and second inertial sensors 12, 13 cannot move relative to the upper limb 15 and the golf club 14, respectively. Here, when mounting the second inertial sensor 13, one of the detection axes of the second inertial sensor 13 is aligned with the direction of the longitudinal axis of the shaft 14a (the direction in which the shaft extends).

The golf swing analysis device 11 has a calculation processing circuit (calculation unit) 16. The first and second inertial sensors 12, 13 are connected to the calculation processing circuit 16. For this connection, a predetermined interface circuit 17 is connected to the calculation processing circuit 16. The interface circuit 17 may be wired to the inertial sensors 12, 13 or wirelessly connected to the inertial sensors 12, 13. The detection signal is inputted to the calculation processing circuit 16 from the inertial sensors 12, 13.

A storage device 18 is connected to the calculation processing circuit 16. In the storage device 18, for example, a golf swing analysis software program 19 and related data are stored. The calculation processing circuit 16 executes the golf swing analysis software program 19 to realize a golf swing analysis method. The storage device 18 includes a DRAM (dynamic random access memory), a large-capacity storage unit, a non-volatile memory or the like. For example, in the DRAM, the golf swing analysis software program 19 is temporarily held when carrying out the golf swing analysis method. In the large-capacity storage unit such as a hard disk drive (HDD), the golf swing analysis software program and data are saved. In the non-volatile memory, a relatively small-capacity program such as BIOS (basic input/output system) and data are stored.

An image processing circuit 21 is connected to the calculation processing circuit 16. The calculation processing circuit 16 sends predetermined image data to the image processing circuit 21. A display device 22 is connected to the image processing circuit 21. For this connection, a predetermined interface circuit (not shown) is connected to the image processing circuit 21. The image processing circuit 21 sends an image signal to the display device 22, according to the image data inputted thereto. An image specified by the image signal is displayed on the screen of the display device 22. As the display device 22, a liquid crystal display or another type of flat panel display is used. Here, the calculation processing circuit 16, the storage device 18 and the image processing circuit 21 are provided, for example, as a computer device.

An input device 23 is connected to the calculation processing circuit 16. The input device 23 has at least alphabetical keys and ten keys. Letter information and numerical value information are inputted to the calculation processing circuit 16 from the input device 23. The input device 23 may include, for example, a keyboard. The combination of the computer device with the keyboard may be replaced, for example, with a smartphone, mobile phone, or tablet PC (personal computer).

2. Motion Analysis Model

Figure 2:
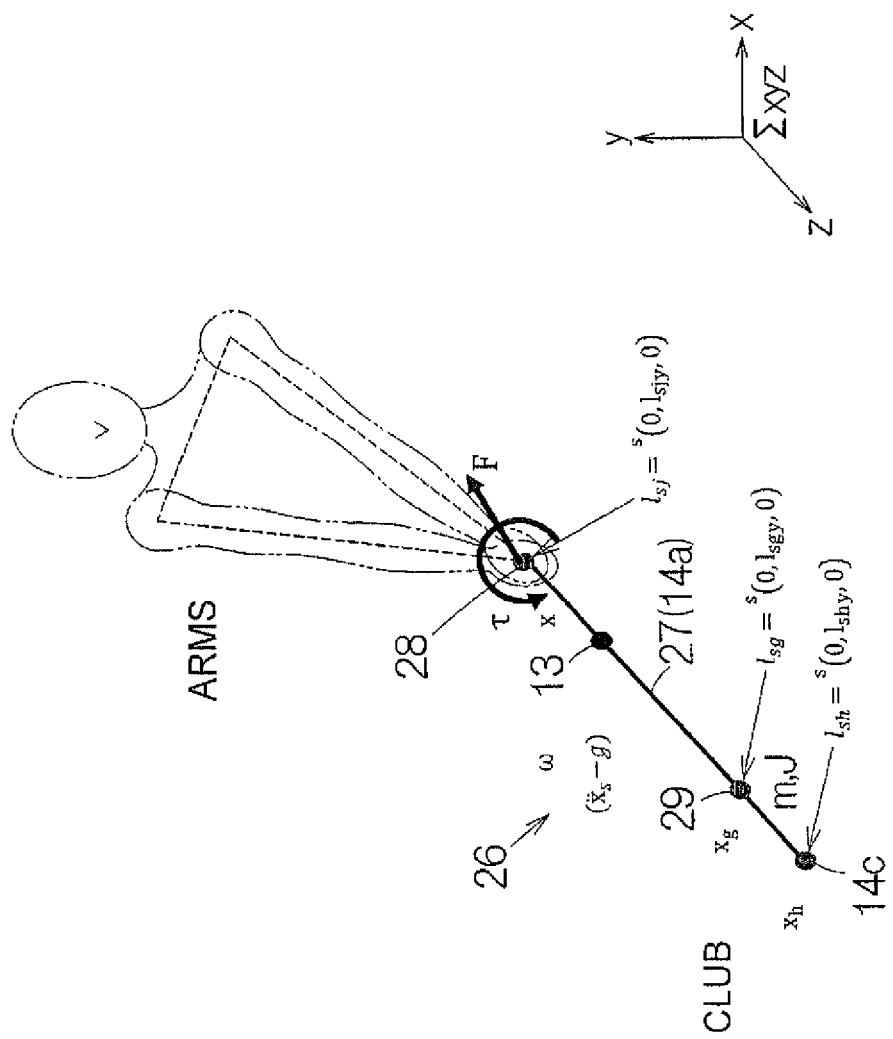
FIG. 2 is a conceptual view schematically showing the relation between a swing model, and a golfer and a golf club.

The calculation processing circuit 16 prescribes an imaginary space. The imaginary space is formed as a three-dimensional space. The three-dimensional space specifies a real space. As shown in FIG. 2, the three-dimensional space has an absolute reference coordinate system (overall coordinate system) $\Sigma_{xyz}$. In the three-dimensional space, a three-dimensional motion analysis model 26 is constructed in accordance with the absolute reference coordinate system $\Sigma_{xyz}$. A bar 27 in the three-dimensional motion analysis model 26 is point-constrained at a support 28 (coordinate x). The bar 27 acts as a pendulum three-dimensionally about the support 28. The position of the support 28 can be moved. Here, according to the absolute reference coordinate system $\Sigma_{xyz}$, the position of the center of gravity 29 of the bar 27 is specified by a coordinate $x_g$ and the position of the club head 14c is specified by a coordinate $x_h$.

The three-dimensional motion analysis model 26 is equivalent to a modeling of the golf club 14 at the time of a swing. The pendulum bar 27 projects the shaft 14a of the golf club 14. The support 28 of the bar 27 projects the grip 14b. The second inertial sensor 13 is fixed on the bar 27. According to the absolute reference coordinate system $\Sigma_{xyz}$, the position of the second inertial sensor 13 is specified by a coordinate $x_s$. The second inertial sensor 13 outputs an acceleration signal and an angular velocity signal. The acceleration signal specifies an acceleration minus the influence of gravitational acceleration g, that is, $(\ddot{X}_s - g)$. The angular velocity signal specifies angular velocities $\omega_1, \omega_2$.

The calculation processing circuit 16 similarly fixes a local coordinate system $\Sigma_s$ on the second inertial sensor 13. The origin of the local coordinate system $\Sigma_s$ is set at the origin of the detection axis of the second inertial sensor 13. The y-axis of the local coordinate system $\Sigma_s$ coincides with the axis of the shaft 14a. The x-axis of the local coordinate system $\Sigma_s$ coincides with the ball hitting direction that is specified by the direction of the face. Therefore, according to the local coordinate system $\Sigma_s$, the position $1_{sj}$ of the support is specified by $(0, 1_{sjy}, 0)$. Similarly, on this local coordinate system $\Sigma_s$, the position $1_{sg}$ of the center of gravity 29 is specified by $(0, 1_{sgy}, 0)$, and the position $1_{sh}$ of the club head 14c is specified by $(0, 1_{shy}, 0)$.

Figure 3:
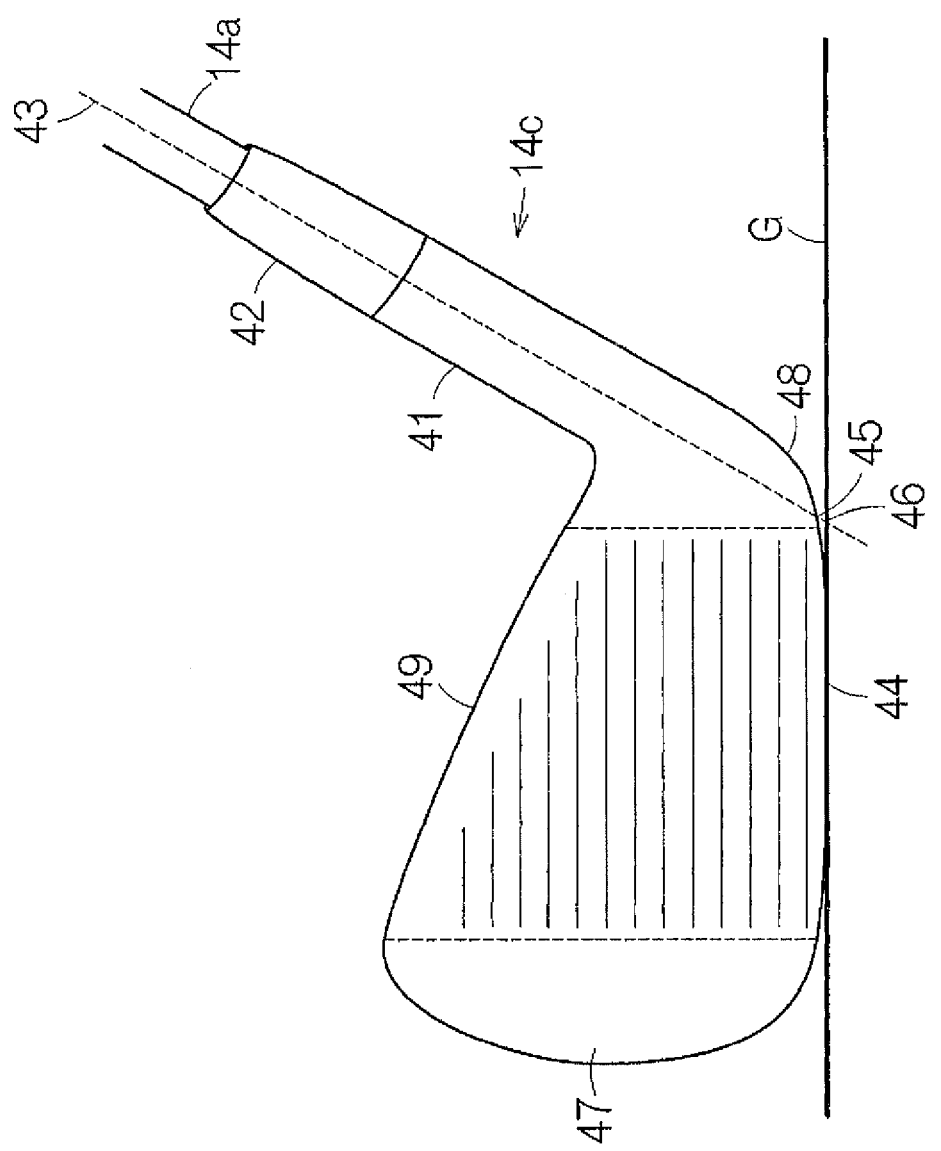
FIG. 3 is a conceptual view of a position of a club head used for a swing model.

As shown in FIG. 3, at the club head 14c, the shaft 14a is inserted in a hosel 41. A ferrule 42 is arranged at the boundary between the hosel 41 and the shaft 14a. The longitudinal axis of the hosel 41 and the ferrule 42 is arranged coaxially with a longitudinal axis 43 of the shaft 14a. The position of the club head 14c may be specified, for example, by a point of intersection 45 between an extension line of the direction of the longitudinal axis (axial line) 43 of the shaft 14a and a sole 44 of the club head 14c. Alternatively, the position of the club head 14c may be specified by a point of intersection 46 between the extension line of the longitudinal axis 43 of the shaft 14a and ground G when the sole 44 of the club head 14c flatly contacts the ground G. Also, unless there is any problem with image forming as described later, the position of the club head 14c may be set by a toe 47 and a heal 48 of the club head 14c, another part on the sole 44, a crown 49, and peripheries thereof. However, it is desirable that the position of the club head 14c is set in the axial direction 43 of the shaft 14a (or on the extension line thereof).

Figure 4:
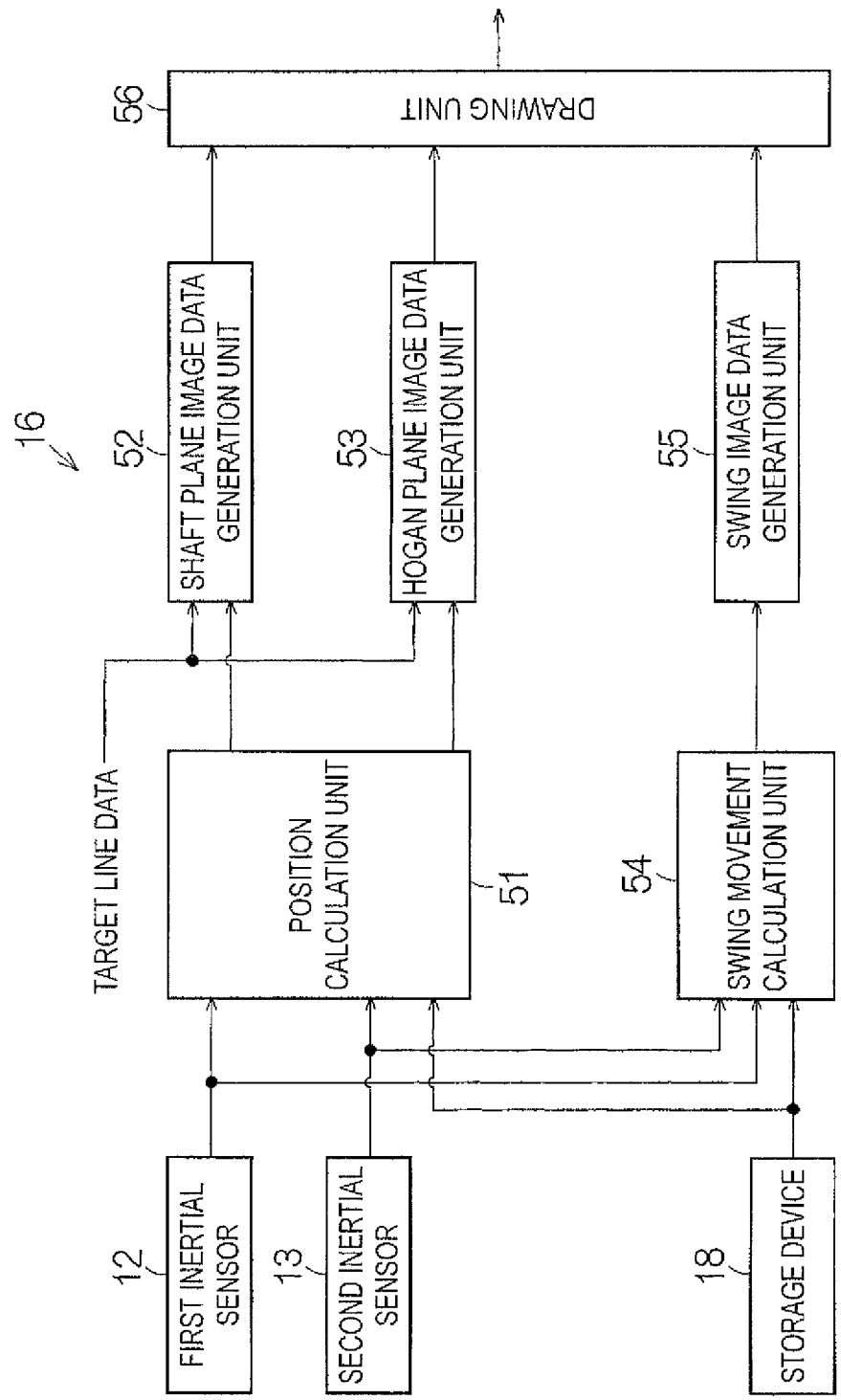
FIG. 4 is a block diagram schematically showing the configuration of a calculation processing circuit according to the first embodiment.

3. Configuration of Calculation Processing Circuit According to First Embodiment FIG. 4 schematically shows the configuration of the calculation processing circuit 16 according to the first embodiment. The calculation processing circuit 16 has a position calculation unit 51. The acceleration signal and the angular velocity signal are inputted to the position calculation unit 51 from the first inertial sensor 12 and the second inertial sensor 13. The position calculation unit 51 calculates the coordinates of the club head 14c, the coordinates of the grip end, and the coordinates of the subject's shoulder according to the absolute reference coordinate system in the imaginary three-dimensional space, at least based on the acceleration signal. The method for calculation will be described later. In this calculation, the position calculation unit 51 acquires various numerical value data including data about length information of the shaft such as club head data and grip end data, and shoulder data. The club head data specifies the position of the club head 14c, for example, according to the output from the second inertial sensor 13. The grip end data specifies the position of the grip end, for example, according to the output from the second inertial sensor 13. Also, in specifying the position of the club head 14c and the position of the grip end, the length of the golf club 14 may be specified and the position of the second inertial sensor 13 may be specified on the golf club 14. The shoulder data specifies the position of the subject's shoulder, for example, according to the output from the first inertial sensor 12. Alternatively, the position of the shoulder may be specified based on length data representing the distance from the first inertial sensor 12 to the subject's shoulder. Also, in specifying the position of the shoulder, the height of the subject and the length of the subject's left arm may be specified and the position of the first inertial sensor 12 may be specified on the arm.

The calculation processing circuit 16 has a shaft plane image data generation unit 52 and a Hogan plane image data generation unit 53. The shaft plane is a plane formed by the direction of the longitudinal axis of the shaft 14a of the golf club 14 when the golfer is at address position (static state) and a target line (ball hitting direction). The Hogan plane is a plane formed by an imaginary line connecting the neck bottom (bottom of the neck) of the golfer and the ball when the golfer is at address position and a target line (ball hitting direction). The Hogan plane can be said to be an imaginary line connecting the golfer's shoulder to the ball since the position of the neck bottom and the position of the shoulder are arrayed substantially on the same straight line if the subject is viewed from the lateral side. The shaft plane image data generation unit 52 and the Hogan plane image data generation unit 53 are connected to the position calculation unit 51. The shaft plane image data generation unit 52 generates three-dimensional image data to visualize a first imaginary plane, that is, the shaft plane in three dimensions, based on the coordinates of the grip end. To generate the three-dimensional image data, the shaft plane image data generation unit 52 refers to target line data. The target line data represents a target line that is a line segment which specifies the ball hitting direction on the absolute reference coordinate system. The target line can also be said to be a direction intersecting with the face side of the club head 14c at address position (in static state). The Hogan plane image data generation unit 53 generates three-dimensional image data to visualize a second imaginary plane, that is, the Hogan plane in three dimensions, based on the coordinates of the subject's shoulder. To generate the three-dimensional image data, the Hogan plane image data generation unit 53 similarly refers to the target line data.

The calculation processing circuit 16 has a swing movement calculation unit 54. The acceleration signal and the angular velocity signal are inputted to the swing movement calculation unit 54 from the first inertial sensor 12 and the second inertial sensor 13. The swing movement calculation unit 54 calculates the movement trajectory of the golf club 14 in a swing, based on the acceleration and the angular velocity.

The calculation processing circuit 16 has a swing image data generation unit 55. The swing image data generation unit 55 is connected to the swing movement calculation unit 54. The swing image data generation unit 55 generates three-dimensional image data to visualize the movement trajectory of the golf club 14 along time axis.

The calculation processing circuit 16 has a drawing unit 56. The drawing unit 56 is connected to the shaft plane image data generation unit 52, the Hogan plane image data generation unit 53 and the swing image data generation unit 55. The drawing unit 56 generates three-dimensional image data to visualize the movement trajectory of the golf club 14 in three dimensions superimposed on the shaft plane and the Hogan plane, based on the three-dimensional image data from the shaft plane image data generation unit 52, the three-dimensional image data from the Hogan plane image data generation unit 53 and the three-dimensional image data from the swing image data generation unit 55.

Figure 5:
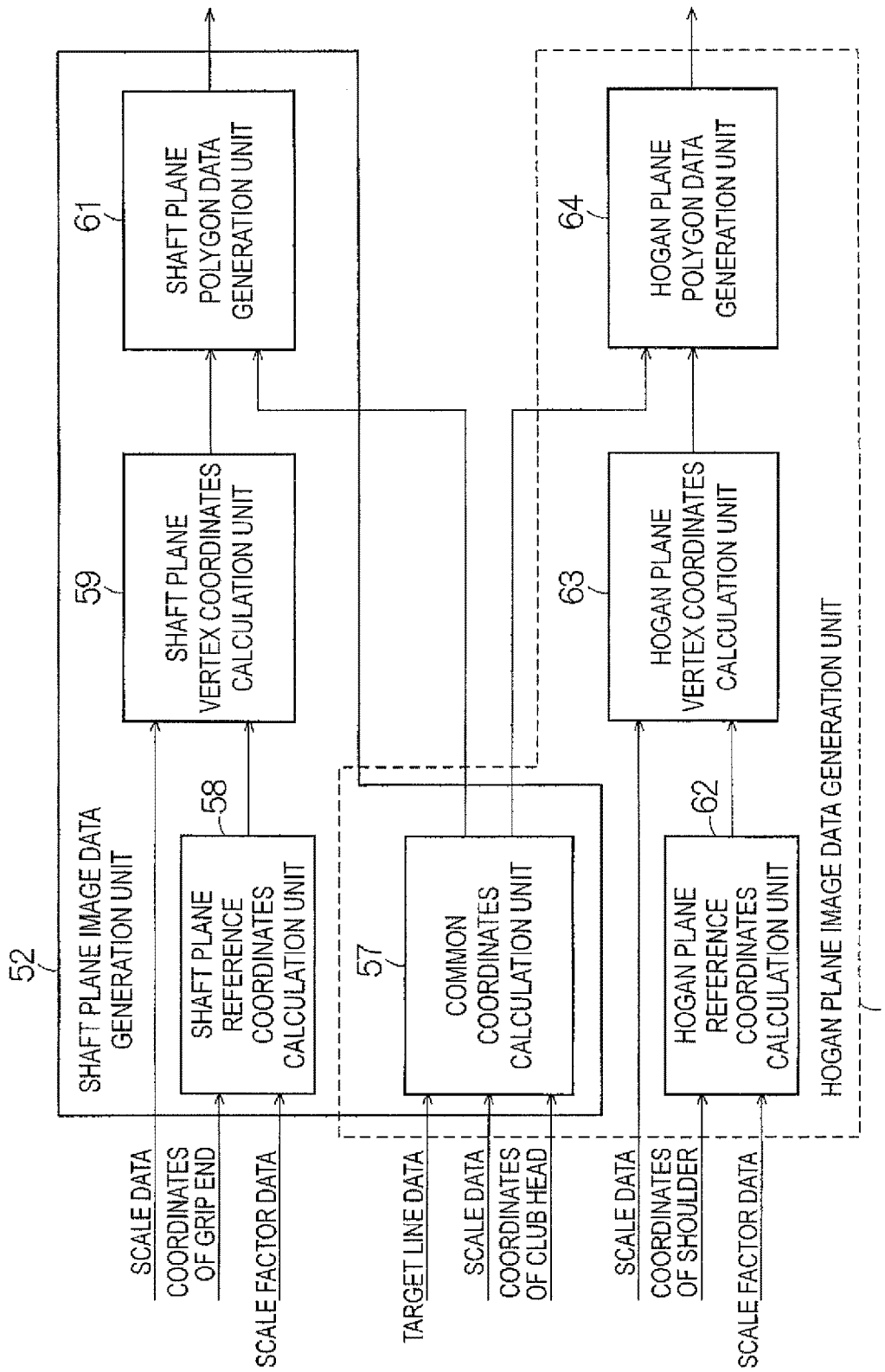
FIG. 5 is a block diagram schematically showing the configuration of a shaft plane image data generation unit and a Hogan plane image data generation unit.

As shown in FIG. 5, the shaft plane image data generation unit 52 has a common coordinates calculation unit 57, a shaft plane reference coordinates calculation unit 58, a shaft plane vertex coordinates calculation unit 59, and a shaft plane polygon data generation unit 61. The common coordinates calculation unit 57 calculates the coordinates of two vertices of the shaft plane, based on the target line data. Details of this calculation will be described later. The shaft plane reference coordinates calculation unit 58 calculates a reference position of the shaft plane on the extension line of the longitudinal axis 43 of the shaft 14a, based on the coordinates of the grip end. The shaft plane vertex coordinates calculation unit 59 is connected to the shaft plane reference coordinates calculation unit 58. The shaft plane vertex coordinates calculation unit 59 calculates the coordinates of two vertices of the shaft plane, based on the calculated reference position of the shaft plane. The shaft plane polygon data generation unit 61 is connected to the shaft plane vertex coordinates calculation unit 59 and the common coordinates calculation unit 57. The shaft plane polygon data generation unit 61 generates polygon data of the shaft plane, based on the coordinates of the four vertices in total that are calculated. The polygon data is equivalent to the three-dimensional image data to visualize the shaft plane in three dimensions.

Similarly, the Hogan plane image data generation unit 53 has the common coordinates calculation unit 57, a Hogan plane reference coordinates calculation unit 62, a Hogan plane vertex coordinates calculation unit 63, and a Hogan plane polygon data generation unit 64. The common coordinates calculation unit 57 calculates the coordinates of two vertices of the Hogan plane, based on the target line data. Here, since the two vertices of the shaft plane and the two vertices of the Hogan plane are different from each other on the target line, the Hogan plane image data generation unit 53 shares the common coordinates calculation unit 57 with the shaft plane image data generation unit 52. The Hogan plane reference coordinates calculation unit 62 calculates a reference position of the Hogan plane on the extension line of the longitudinal axis of the left arm, based on the coordinates of the shoulder. The Hogan plane vertex coordinates calculation unit 63 is connected to the Hogan plane reference coordinates calculation unit 62. The Hogan plane vertex coordinates calculation unit 63 calculates the coordinates of two vertices of the Hogan plane, based on the calculated reference position of the Hogan plane. The Hogan plane polygon data generation unit 64 is connected to the Hogan plane vertex coordinates calculation unit 63 and the common coordinates calculation unit 57. The Hogan plane polygon data generation unit 64 generates polygon data of the Hogan plane, based on the coordinates of the four points in total that are calculated. The polygon data is equivalent to the three-dimensional image data to visualize the Hogan plane in three dimensions.

Figure 6:
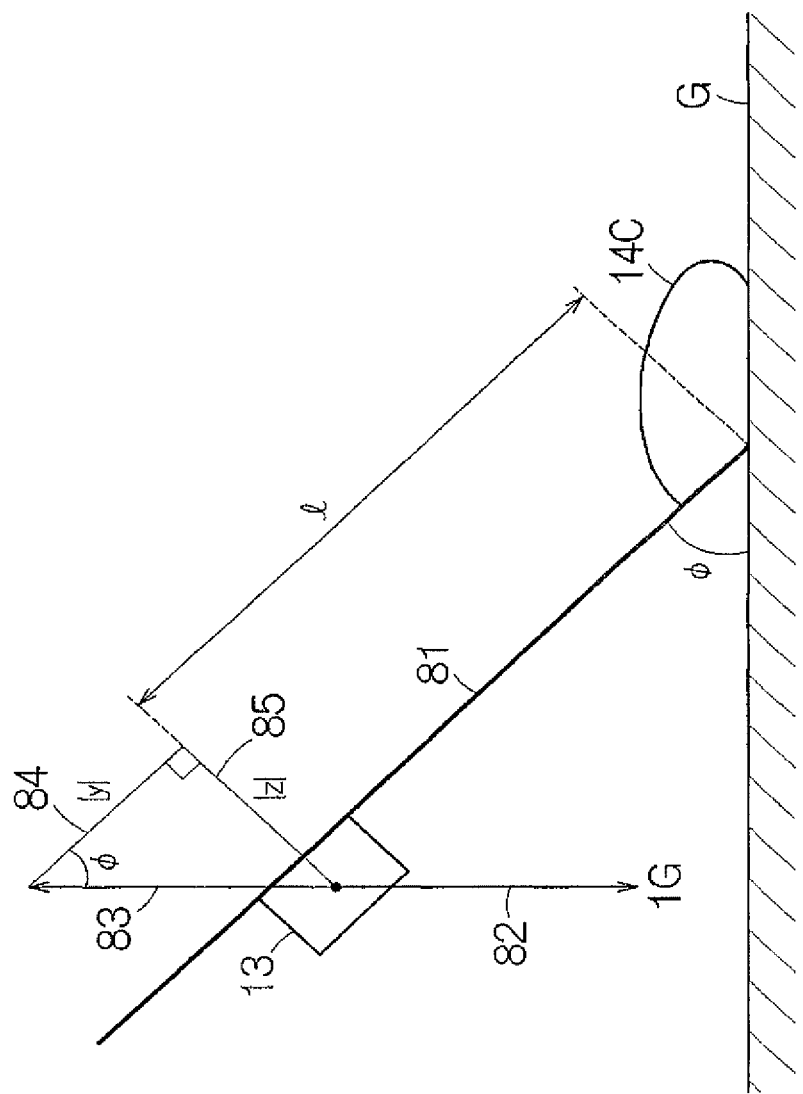
FIG. 6 is a conceptual view schematically showing a method for calculating a line segment representing the longitudinal axis of a shaft.

Now, FIG. 6 shows an example of the way to find a line segment (first line segment) 81 forming the shaft plane (first imaginary plane) and representing the direction in which the longitudinal axis 43 of the shaft 14*a* extends. The line segment 81 is found from the output from the acceleration sensor of the second inertial sensor 13 installed on the shaft 14*a* of the golf club 14 in a static posture. The acceleration sensor of the second inertial sensor 13 has plural detection axes and one of the detection axes is fixed on the shaft 14*a* so as to coincide with the direction of the longitudinal axis of the shaft 14*a*. An upward force 83 opposite to downward gravity 82 acts on the second inertial sensor 13. The acceleration sensor of the second inertial sensor 13 resolves the upward force 83 acting in response to the gravity 82 into a first force component 84 along the direction of the longitudinal axis of the shaft 14*a* and a second force component 85 orthogonal to the direction of the longitudinal axis of the shaft 14*a* and measures these force components. Based on the resolved force components 84, 85, the angle of inclination φ of the direction of the longitudinal axis of the shaft 14*a* with respect to the direction of gravity is found, using the triangular function. Here, the force component 84 is equivalent to the acceleration vector (=|y|) in the direction of the longitudinal axis of the shaft (y-axis direction). The force component 85 is equivalent to the acceleration vector (=|z|) in a direction orthogonal to the former acceleration vector (for example, z-axis direction).

$$\varphi = \tan^{-1} \frac{|z|}{|y|}$$

Next, the line segment 81 is found, based on the length information of the shaft 14*a* that is inputted in advance and the angle of inclination φ in the direction of the longitudinal axis of the shaft 14*a* that is found before. Thus, the position coordinates of the club head 14*c* in the imaginary three-dimensional space are specified. As the length information of the shaft 14*a*, the distance from the position of the second inertial sensor 13 to an end of the club head 14*c* may be used. The plane including the line segment 81 and the target line (ball hitting direction), later described, is specified as the shaft plane.

To find the Hogan plane (second imaginary plane), though not shown, the acceleration sensor of the first inertial sensor 12 installed on the subject's arm is used to find the inclination of the subject's arm in a static posture with respect to the direction of gravity, and a line segment forming the Hogan plane is calculated based on the length information of the subject's arm that is inputted in advance and the angle of inclination of the arm, as in the case of the above line segment 81 of the shaft plane.

Figure 7:
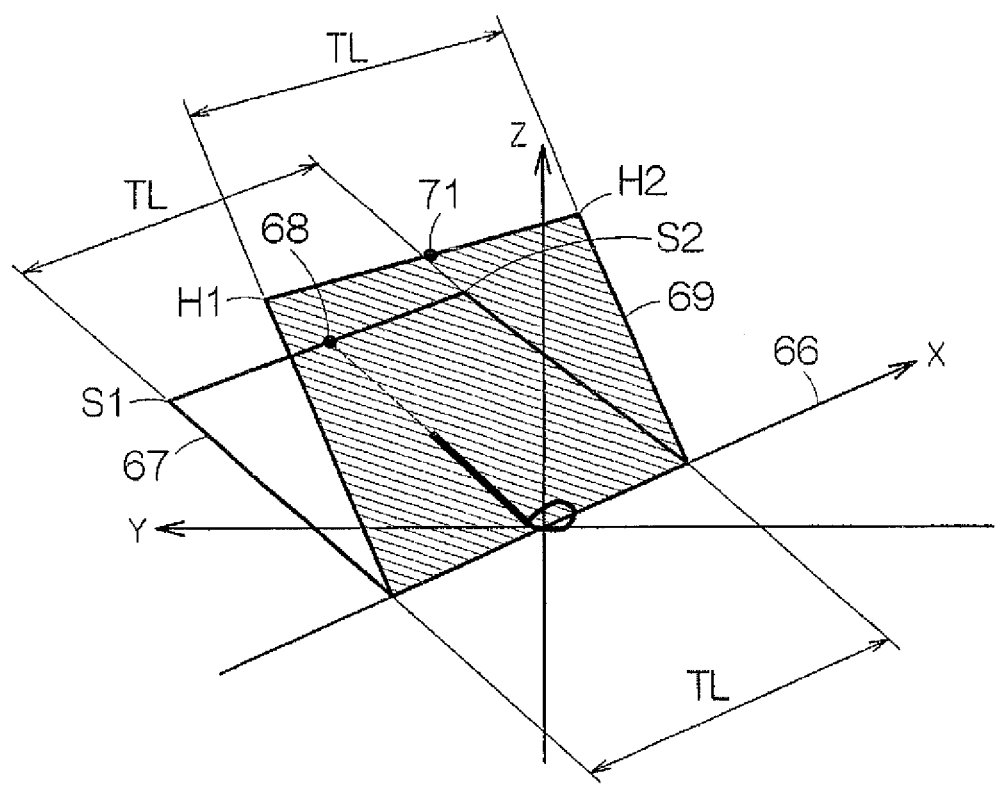
FIG. 7 is a conceptual view of the shaft plane and the Hogan plane.
Figure 8:
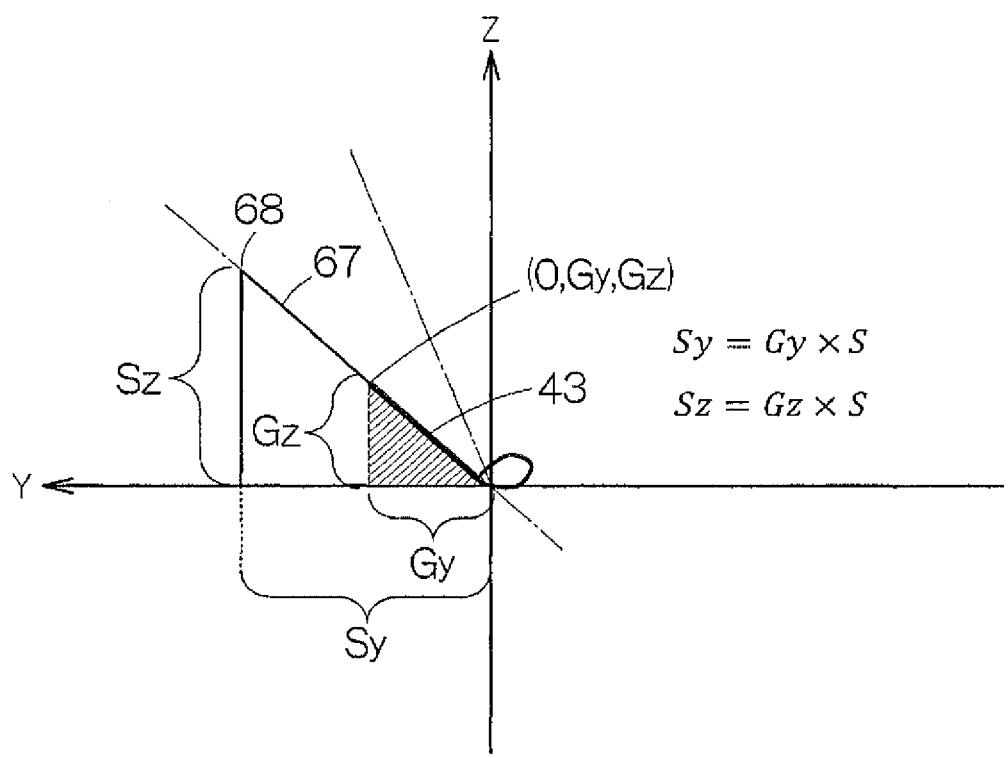
FIG. 8 is a conceptual view showing a method for generating the shaft plane.
Figure 9:
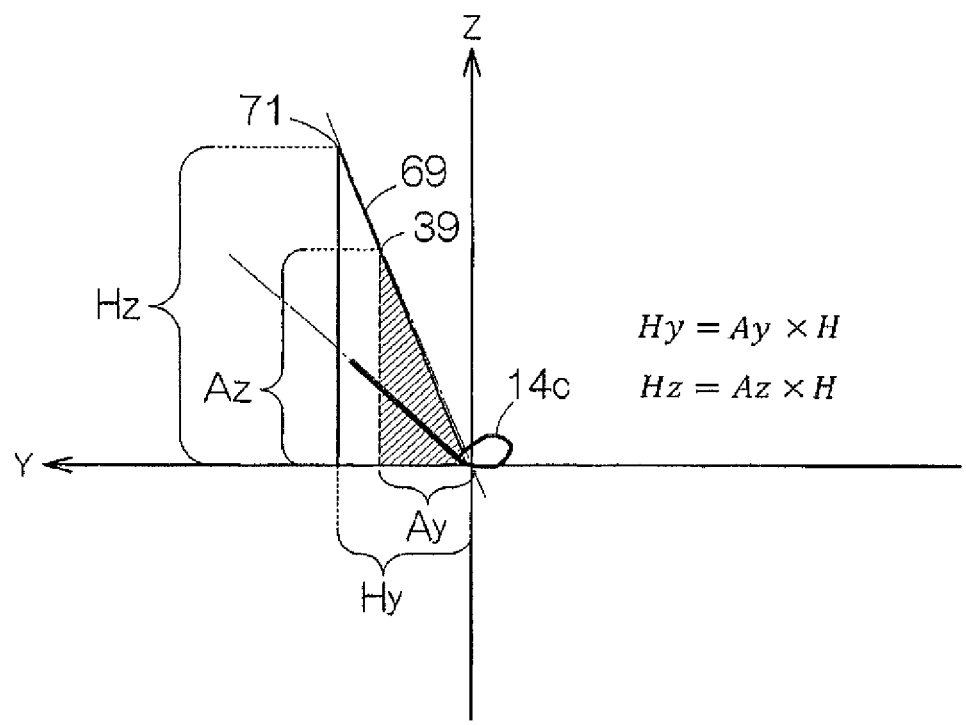
FIG. 9 is a conceptual view showing a method for generating the Hogan plane.

Next, the shaft plane image data generation unit 52 and the Hogan plane image data generation unit 53 will be described in detail with reference to FIGS. 7 to 9. The common coordinates calculation unit 57 refers to the coordinates of the club head 14*c* and scale data, when calculating the coordinates of the vertices. As clear from FIG. 7, the scale data specifies a numerical value TL indicating the size of a shaft plane 67 on a target line 66. The numerical value TL is set as such a size that an entire swing movement falls within the shaft plane 67 when the swing movement is projected on the shaft plane 67. When calculating the coordinates of the vertices, the common coordinates calculation unit 57 can align the position of the club head 14*c* with the target line 66, by comparing the coordinates of the club head 14*c* with the target line 66.

The shaft plane reference coordinates calculation unit 58 refers to first scale factor data when calculating the reference position. As shown in FIG. 8, the first scale factor specifies a magnification rate S of the longitudinal axis 43 of the shaft 14*a*. In accordance with the magnification rates, an extension line of the longitudinal axis 43 of the shaft 14*a* is specified beyond the grip end (0, Gy, Gz). At the end of the extension line, a reference position 68 (0, Sy, Sz) of the shaft plane 67 is specified. The magnification rate S of the longitudinal axis 43 is set at such a numerical value that an entire swing movement falls within the shaft plane 67 when the swing movement is projected on the shaft plane 67.

The shaft plane vertex coordinates calculation unit 59 refers to the scale data when calculating the coordinates of the vertices. As clear form FIG. 7, a line segment with a length TL passing through the reference position 68 of the shaft plane 67 is specified. The coordinates S1, S2 of the vertices are provided at both ends of this line segment.

The Hogan plane reference coordinates calculation unit 62 refers to second scale factor data when calculating the reference position. As shown in FIG. 9, the second scale factor data specifies a magnification rate H of the line segment connecting the shoulder and the club head 14*c*. In accordance with the magnification rate H, an extension line of the line segment is specified beyond the shoulder. The magnification rate H of the line segment is set at such a numerical value that an entire swing movement falls within a Hogan plane 69 when the swing movement is projected on the Hogan plane 69. In FIG. 9, in specifying the magnification rate H, the shoulder is projected on a yz plane including the longitudinal axis 43 of the shaft 14*a*. A reference position 71 (0, Hy, Hz) of the Hogan plane 69 is specified, based on the position of the projection. Therefore, the reference position 71 (0, Hy, Hz) is specified within the yz plane.

The Hogan plane vertex coordinates calculation unit 63 refers to the scale data when calculating the coordinates of the vertices. As clear from FIG. 7, a line segment with a length TL passing through the reference position 71 of the Hogan plane 69 is specified. The coordinates of the vertices H1, H2 are provided at both ends of the line segment.

4. Operation of Golf Swing Analysis Device

The operation of the golf swing analysis device 11 will be described briefly. First, a golfer's golf swing is measured. Before the measurement, necessary information is inputted to the calculation processing circuit 16 from the input device 23. The inputted information is managed, for example, under a specific identifier. The identifier may identify a specific golfer.

Before the measurement, the first and second inertial sensors 12, 13 are mounted on the golf club 14 and the golfer's upper limb 15. If the golfer is right-handed, the left arm may be selected as the upper limb 15. This is because the left arm will bend less at the elbow from the start of a golf swing to the impact. The first and second inertial sensors 12, 13 are fixed in such a way that the first and second inertial sensors 12, 13 cannot be displaced relative to the golf club 14 and the upper limb 15.

The measurement by the first and second inertial sensors 12, 13 is started before the execution of a golf swing. At the start of the measurement, the first and second inertial sensors 12, 13 are set in predetermined positions and postures. During the measurement, synchronization is secured between the first and second inertial sensors 12, 13. The first and second inertial sensors 12, 13 continuously measure acceleration and angular velocity at a specific sampling interval. The sampling interval prescribes the resolution of the measurement. Detection signals from the first and second inertial sensors 12, 13 may be sent in real time to the calculation processing circuit 16 or may be temporarily stored in built-in storage devices in the first and second inertial sensors 12, 13. In the latter case, the detection signals may be sent to the calculation processing circuit 16 via wired or wireless transmission after the end of the golf swing.

In the measurement of a golf swing, the subject first takes an address posture. When in the address posture, the subject reproduces the posture at the moment of impact. As a result, the posture at the moment of impact is extracted from a series of movements called "golf swing". At this point, the golf club 14 is held in a static posture. The posture of the subject's upper limb 15 is fixed. Detection signals at address are outputted from the first and second inertial sensors 12, 13. Here, if the static postures of the golf club 14 and the upper limb 15 are maintained for a predetermined time period, the subject may be notified of the completion of the measurement at address. Such a notification can use, for example, an auditory signal. Subsequently, the subject carries out a swing movement. A golf swing starts with the take back, then goes through the backswing, downswing and impact, and reaches the follow and finish. During the swing movement, detection signals are outputted from the first and second inertial sensors 12, 13.

Figure 10:
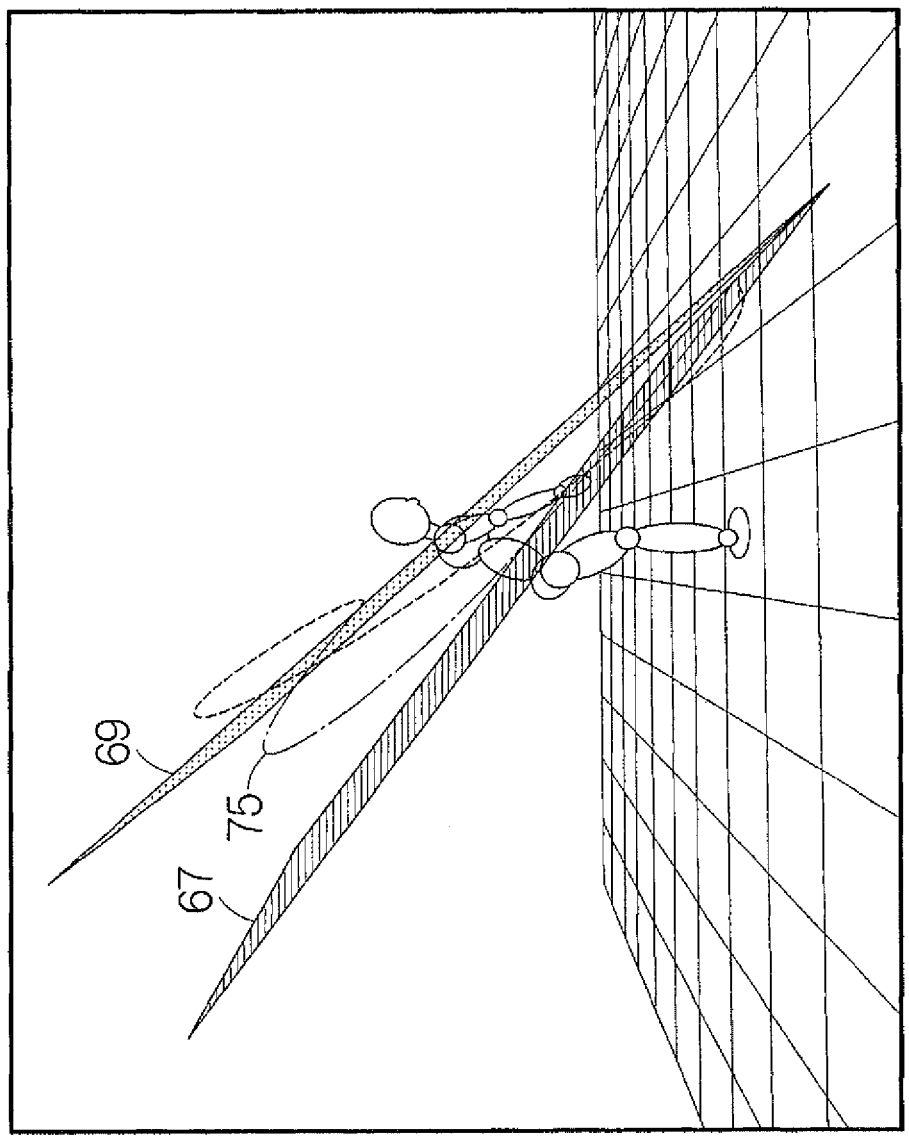
FIG. 10 is a conceptual view schematically showing a specific example of an image according to an analysis result.

In response to the reception of the detection signals, the calculation processing circuit 16 executes analysis of the golf swing. The analysis may be carried out during a period from the start of the take back to the end of the follow, or may be carried out during a period from the start of the take back to the impact. The shaft plane image data generation unit 52 of the calculation processing circuit 16 calculates the shaft plane based on the detection signal from the acceleration sensor at address. The Hogan plane image data generation unit 53 of the calculation processing circuit 16 calculates the Hogan plane based on the detection signal from the acceleration sensor at address. The swing image data generation unit 55 of the calculation processing circuit 16 calculates the movement trajectories of the golf club 14 and the upper limb 15 based on the detection signal at the time of the swing movement. As shown in FIG. 10, in accordance with the calculation of the shaft plane and the Hogan plane and the calculation of the trajectories of the golf club 14 and the upper limb 15, the drawing unit 56 of the calculation processing circuit 16 generates three-dimensional image data to visualize the trajectories 75 of the golf club 14 and the upper limb 15 in three dimensions superimposed on the shaft plane 67 and the Hogan plane 69. The three-dimensional image data is supplied to the image processing circuit 21. As a result, a desired image is displayed on the screen of the display device 22. Thus, the subject can use the information whether the golf club at impact is within an area (V-zone) between the shaft plane 67 and the Hogan plane 69 at address, as an indicator of good or bad ball hitting.

Here, the target line 66 is calculated based on the detection signal at address. In this calculation, it is preferable that one of the plural detection axes of the second inertial sensor 13 is aligned in advance with the ball hitting direction (x-axis in FIG. 7) specified in the direction of the face. Therefore, when the coordinates of the club head 14*c* are specified at address, the target line 66 is specified based on the parallel displacement of the second inertial sensor 13 in the x-axis direction. However, the target line 66 may be specified by other methods. Also, as another measure, the target line 66 may be specified using the exterior product of the acceleration vector in the direction of the longitudinal axis of the golf club and the acceleration vector in the direction of gravitational acceleration.

The first and second inertial sensors 12, 13 output a detection signal from the acceleration sensor in accordance with the postures of the golf club 14 and the upper limb 15. In response to the detection signal from the acceleration sensor, the shaft plane 67 and the Hogan plane 69 are specified by the above method. The shaft plane 67 can draw an imaginary trajectory of the golf club 14 swung in a golf swing. The trajectory of the golf club 14 in the golf swing is observed in comparison with the imaginary trajectory. Similarly, the trajectory of the golf club 14 in the swing is observed in comparison with the Hogan plane 69. Based on the trajectory of the golf club 14, the subject's swing movement is analyzed. Thus, a clear indicator is provided with respect to the motion called "golf swing". Meanwhile, the gyro sensor is necessary in order to calculate the swing trajectory of the golf club but may be used according to need as a supplementary measure in the calculation of the shaft plane 67 and the Hogan plane 69 in a static posture.

As described above, the shaft plane 67 and the Hogan plane 69 are presented visually in a three-dimensional space to the subject. In accordance with the presentation of the shaft plane 67 and the Hogan plane 69, the subject can clearly imagine the imaginary trajectory of the golf club 14.

Based on the imaginary trajectory in his/her mind, the subject can carry out a series of movements called "golf swing". Thus, good improvement can be added to the movements of golf swing.

Moreover, the shaft plane 67 and the Hogan plane 69, and the trajectory of the golf club 14 in a swing are simultaneously presented in a three-dimensional space to the subject. The subject can visually compare his/her own swing with the shaft plane 67 and the Hogan plane 69. For example, if change and observation of the form is repeated, good improvement can be added to the form of the golf swing through trial and error.

5. Configuration of Golf Swing Analysis According to Second Embodiment

Figure 11:
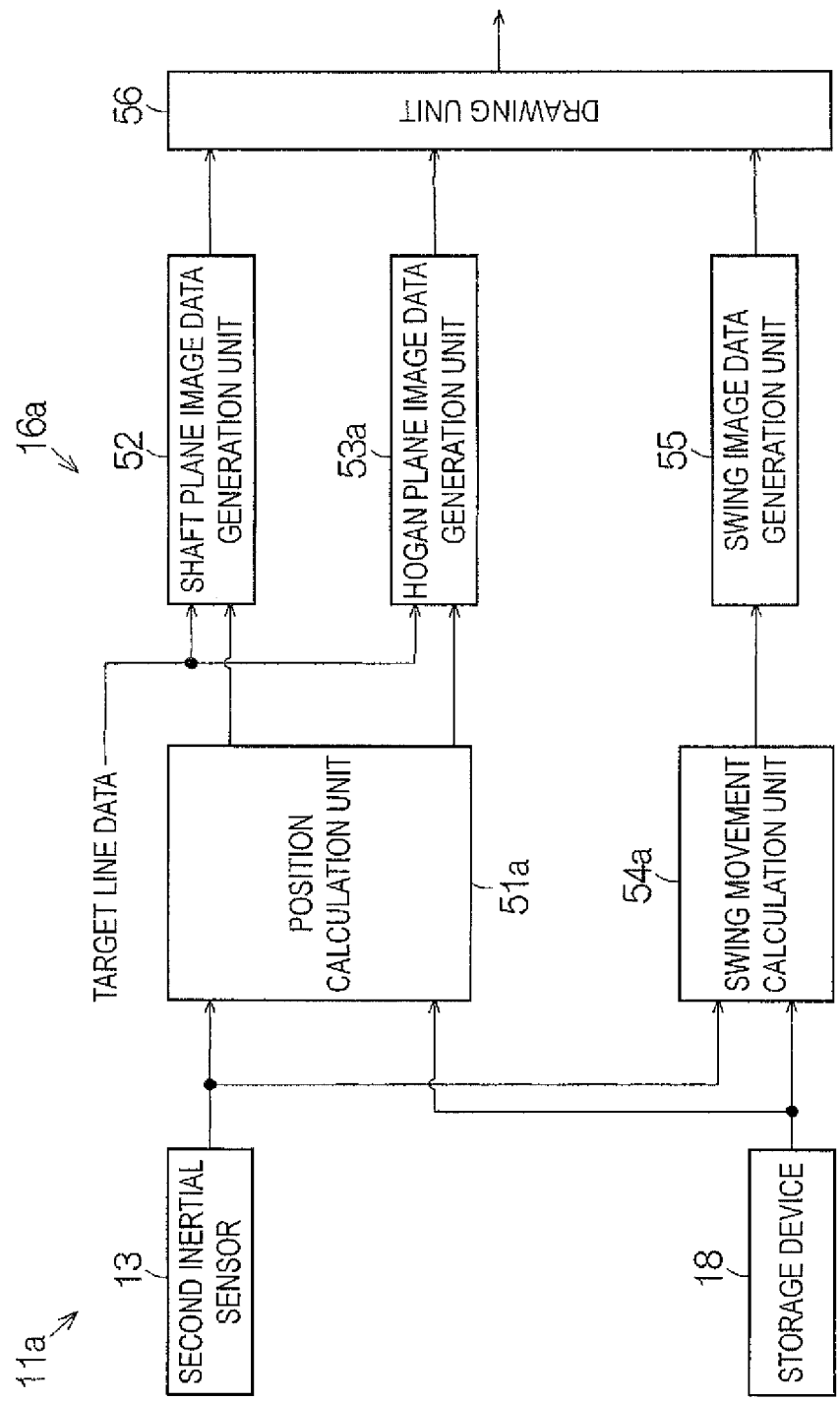
FIG. 11 is a block diagram schematically showing the configuration of a calculation processing circuit of a golf swing analysis device according to a second embodiment.

FIG. 11 schematically shows the configuration of a golf swing analysis device 11a according to a second embodiment. In this golf swing analysis device 11a, compared with the golf swing analysis device 11 according to the first embodiment, the first inertial sensor 12 is omitted. That is, a single inertial sensor, that is, the second inertial sensor 13 is used in the analysis of a golf swing. A calculation processing circuit 16a replaces the calculation processing circuit 16 according to the first embodiment. A position calculation unit 51a may calculate the coordinates of the club head 14c and the coordinates of the grip end, according to the absolute reference coordinates in the imaginary three-dimensional space. A swing movement calculation unit 54a may calculate the displacement of the subject's arm or the club head, according to the absolute reference coordinates.

Figure 12:
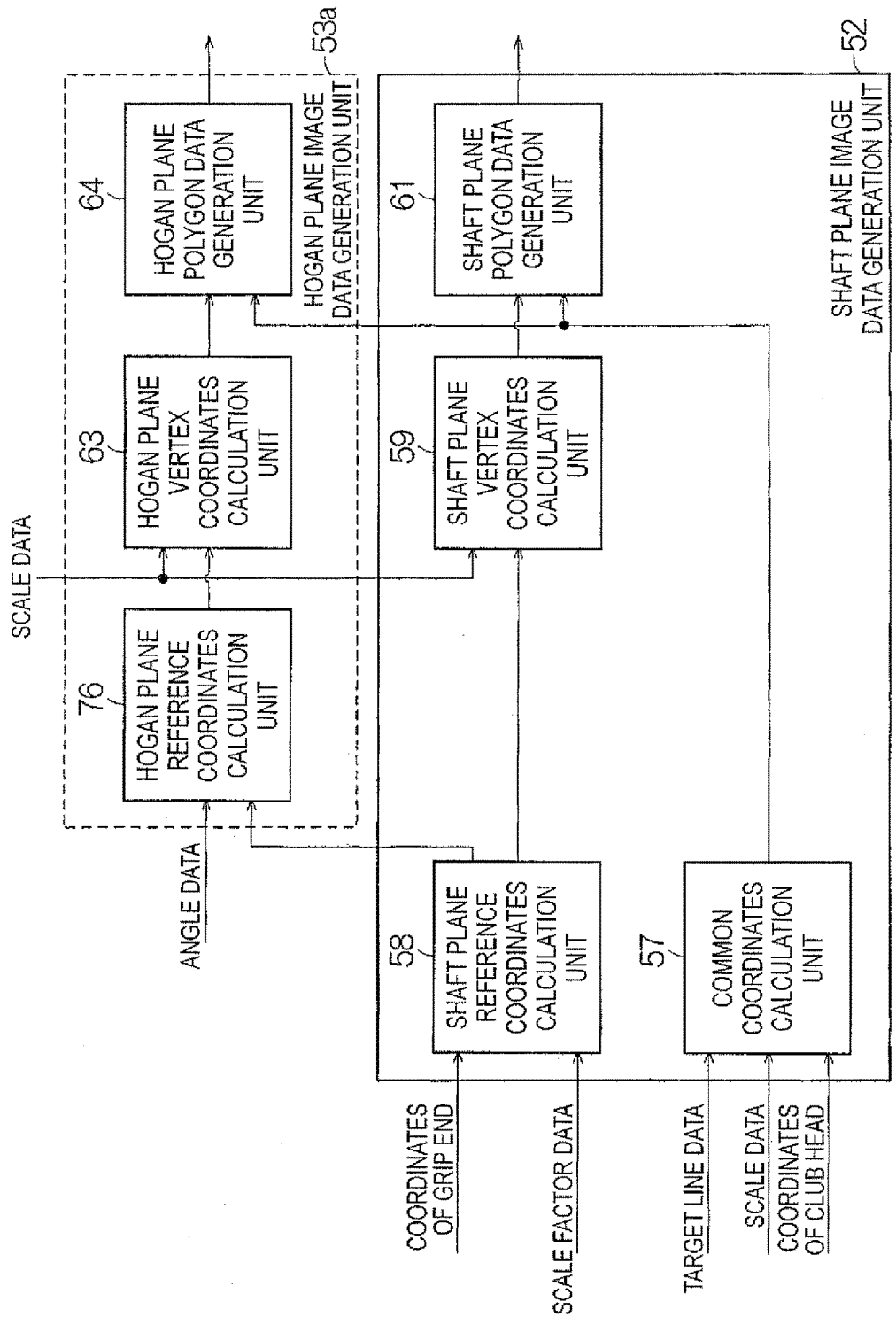
FIG. 12 is a block diagram schematically showing the configuration of a shaft plane image data generation unit and a Hogan plane image data generation unit.

As shown in FIG. 12, the shaft plane image data generation unit 52 is configured similarly to the foregoing configuration. Meanwhile, a Hogan plane reference coordinates calculation unit 76 of a Hogan plane image data generation unit 53a is connected to the shaft plane reference coordinates calculation unit 58. The Hogan plane reference coordinates calculation unit 76 calculates a reference position of the Hogan plane based on the reference position of the shaft plane 67. In this calculation, the Hogan plane reference coordinates calculation unit 76 refers to angle data. The angle data may be stored in the storage device 18 in advance. Based on the calculated reference position, similarly to the foregoing embodiment, the Hogan plane vertex coordinates calculation unit 63 calculates two vertices of the Hogan plane 69.

Figure 13:
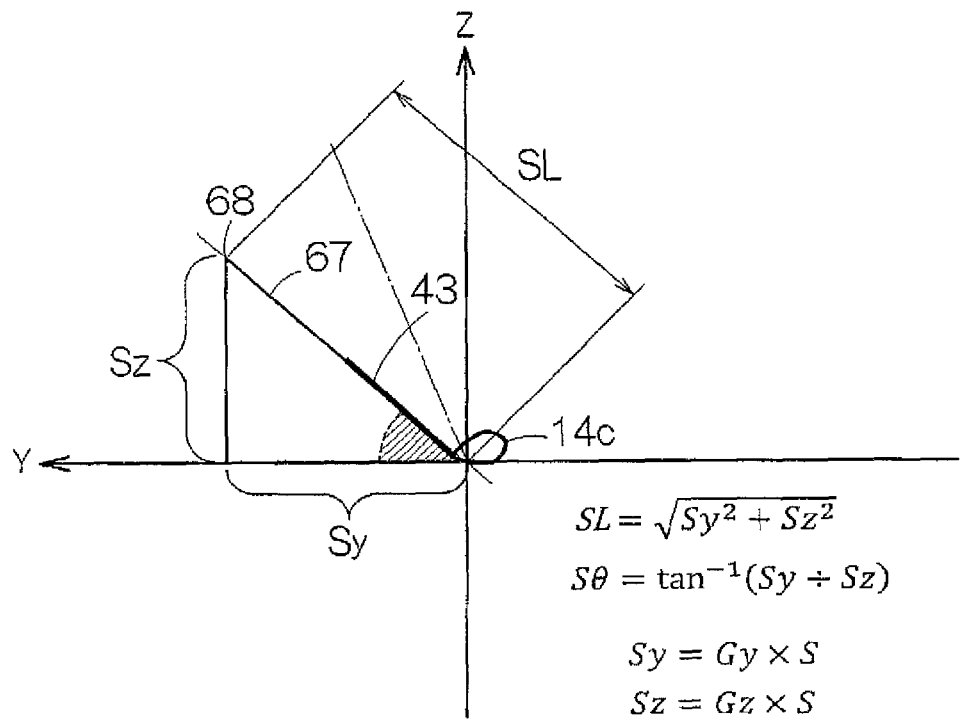
FIG. 13 is a conceptual view showing a method for generating the shaft plane.

As shown in FIG. 13, when calculating the reference position (0, Hy, Hz) of the Hogan plane, the length SL and the angle Sθ of the shaft plane 67 are sent to the Hogan plane reference coordinates calculation unit 76. The length SL and the angle Sθ are calculated based on the coordinates (0, Sy, Sz) of the reference position 68 of the shaft plane 67. These may be calculated by the shaft plane reference coordinates calculation unit 58 or by the Hogan plane reference coordinates calculation unit 76.

Figure 14:
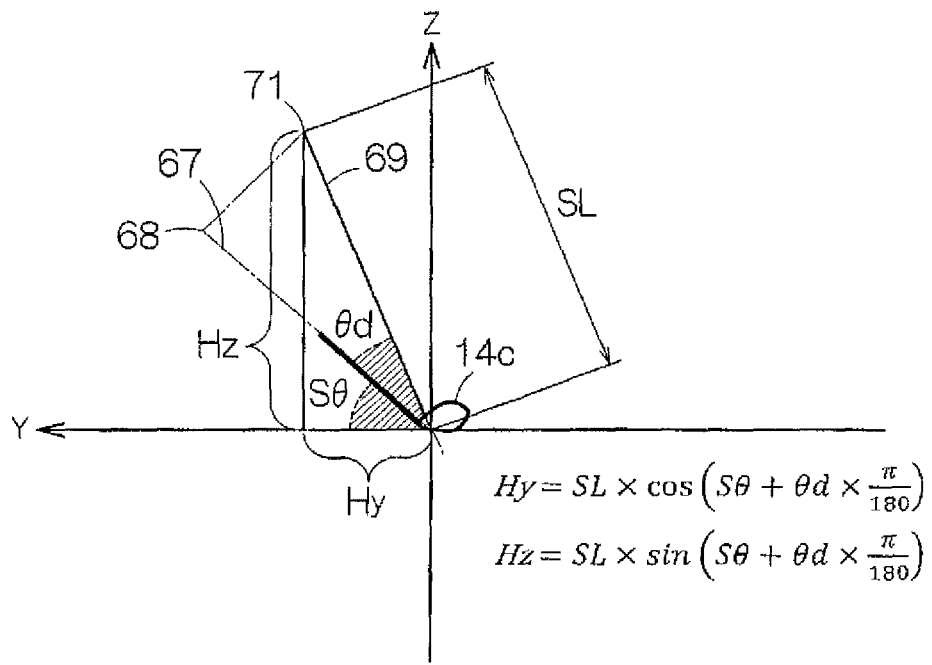
FIG. 14 is a conceptual view showing a method for generating the Hogan plane.

As shown in FIG. 14, the Hogan plane reference coordinates calculation unit 76 rotates the reference position 68 of the shaft plane 67 about the target line 66. The angle θd of this rotation is specified by the angle data. The reference position (0, Hy, Hz) of the Hogan plane 69 is obtained in accordance with the rotation. Thus, according to the golf swing analysis device 11a, analysis of a golf swing is realized with the single inertial sensor (second inertial sensor 13).

In the above embodiments, the individual function blocks of the calculation processing circuits 16, 16a are realized in accordance with the execution of the golf swing analysis software program 19. However, the individual function blocks may be realized by hardware without depending on software processing. Moreover, the golf swing analysis devices 11, 11a may also be applied to swing analysis of other sporting gears held and swung by the hand (for example, a tennis racket or table tennis racket. In such cases, an imaginary plane equivalent to the shaft plane may be used in swing analysis.

While the embodiments are described above in detail, a person skilled in the art can readily understand that various modifications can be made without substantially departing from the new matters and advantageous effects of the invention. Therefore, all such modifications are included in the scope of the invention. For example, in the specification and drawings, a term described along with a different term with a broader meaning or the same meaning at least once can be replaced with the different term in any part of the specification and drawings. Also, the configurations and operations of the first and second inertial sensors 12, 13, the golf club 14, the grip 14b, the club head 14c, the calculation processing circuits 16, 16a and the like are not limited to those described in the embodiments, and various modifications can be made. For example, while a sporting gear such as a golf club having a ball hitting surface and a shaft part is used as an example in the description of the invention, the shaft part need not be in the form of a straight line and the invention can also be applied to a sporting gear that is curved or bent in the direction of the longitudinal axis. Also, while a golf swing is used as an example in the description of the invention, the concept of the invention can be applied to other sports where a ball is hit with a sporting gear, such as tennis or baseball, so as to provide the subject with an indicator of a good or bad swing.

The entire disclosure of Japanese Patent Application No. 2013-130652, filed Jun. 21, 2013 is expressly incorporated by reference herein.

What is claimed is:

1. A motion analysis device, comprising:
    a calculation unit that uses an output of an inertial sensor that measures a swing of a sporting gear to: (i) specify a first plane including (a) a first line that extends in an extending direction of a shaft portion of the sporting gear in a static state of the sporting gear; and (b) a second line showing a ball-hitting direction; and (ii) calculate a trajectory of the swing of the sporting gear; and (iii) calculate an inclination, with respect to a direction of gravity, of the shaft portion of the sporting gear using the output from the inertial sensor in the static state; and
    an output device that outputs an image of: (i) the first plane calculated by the calculation unit; and (ii) the swing trajectory of the sporting gear, so that a user of the sporting gear can view the image of the swing of the sporting gear, the swing trajectory of the sporting gear being different between a back swing and a down swing of the sporting gear, wherein:
        the calculation unit uses the output of the inertial sensor to specify a second plane including: (a) a third line connecting a neck or a shoulder of a user of the sporting gear in a static posture of the user to a ball-hitting position; and (b) the second line showing the ball-hitting direction,
        the first plane is displayed separately from the second plane, and
        the image is used as an indication of good or bad ball hitting.

2. The calculation processing circuit as set forth in claim 1, wherein:
the output of the inertial sensor includes an output of an acceleration sensor, and
the calculation unit further calculates the first line using the inclination and information on a length of the shaft portion.

3. The calculation processing circuit as set forth in claim 1, wherein:
the second line extends in a direction crossing a ball-hitting surface of the sporting gear.

4. The calculation processing circuit as set forth in claim 1, wherein:
the second line extends in a direction orthogonal to the ball-hitting surface of the sporting gear.

5. The calculation processing circuit as set forth in claim 1, wherein:
a second plane is calculated by rotating the first plane about the second line as a rotation axis.

6. The calculation processing circuit as set forth in claim 1, wherein:
the second plane is further calculated, and the first and second planes cross each other at the second line and form a specified angle.

7. A motion analysis device, comprising:
a calculation unit that uses an output of an inertial sensor that measures a swing of a sporting gear to: (i) specify a first plane including (a) a first line connecting a neck or a shoulder of a user of the sporting gear in a static posture of the user in a ball-hitting position; (ii) a second line showing a ball-hitting direction; and (iii) calculate an inclination, with respect to a direction of gravity, of a shaft portion of the sporting gear using the output from the inertial sensor in the static state; and
an output device that outputs an image of: (i) the first plane calculated by the calculation unit and (ii) the swing trajectory of the sporting gear, so that the user of the sporting gear can view the image of the swing of the sporting gear, the swing trajectory of the sporting gear being different between a back swing and a down swing of the sporting gear, wherein:
the calculation unit uses the output of the inertial sensor to specify a second plane including: (a) a first line that extends in an extending direction of a shaft portion of the sporting gear in a static state of the sporting gear; and (b) a second line showing a ball-hitting direction,
the first plane is displayed separately from the second plane, and
the image is used as an indication of good or bad ball hitting.

8. The calculation processing circuit as set forth in claim 7, wherein:
the output of the inertial sensor includes an output of an acceleration sensor, and
the calculation unit further calculates an inclination, with respect to a direction of gravity, of a direction in which an arm of the user extends, using the output from the acceleration sensor in the static posture; estimates a position of the neck or the shoulder of the user using the inclination and information of a length of the arm of the user; and calculates the first line, based on the estimate.

9. The calculation processing circuit as set forth in claim 7, wherein:
the second line extends in a direction crossing a ball-hitting surface of the sporting gear.

10. The calculation processing circuit as set forth in claim 7, wherein:
the second line extends in a direction orthogonal to a ball-hitting surface of the sporting gear.

11. A motion analysis device, comprising:
a first calculation unit that uses an output of an inertial sensor that measures a swing of a sporting gear to: (i) specify a first plane including (a) a first line that extends in an extending direction of a shaft portion of the sporting gear in a static state of the sporting gear; and (b) a second line showing a ball-hitting direction; (ii) calculate a trajectory of the swing of the sporting gear, the swing trajectory of the sporting gear being different between a back swing and a down swing of the sporting gear; and (iii) calculate an inclination, with respect to a direction of gravity, of the shaft portion of the sporting gear using the output from the inertial sensor in the static state; and
a second calculation unit that uses the output of the inertial sensor to specify a second plane including: (a) a third line connecting a neck or a shoulder of a user of the sporting gear in a static posture of the user to a ball-hitting position; and (b) the second line showing the ball-hitting direction; and
an output device that outputs an image of the first plane and the second plane calculated by the first calculation unit and the second calculation unit, so that a user of the sporting gear can view the image of the swing of the sporting gear, wherein:
the calculation unit uses the output of the inertial sensor to specify a second plane including: (a) a third line connecting a neck or a shoulder of a user of the sporting gear in a static posture of the user to a ball-hitting position; and (b) the second line showing the ball-hitting direction,
the first plane is displayed separately from the second plane, and
the image is used as an indication of good or bad ball hitting.

12. The calculation processing circuit as set forth in claim 11, wherein:
the output of the inertial sensor includes an output of an acceleration sensor, and
the first calculation unit further calculates an inclination, with respect to a direction of gravity, of the shaft portion of the sporting gear using the output from the acceleration sensor in the static state, and obtains the first line using the inclination and information on a length of the shaft portion.

13. The calculation processing circuit as set forth in claim 11, wherein:
the output of the inertial sensor includes an output of an acceleration sensor, and
the second calculation unit calculates an inclination, with respect to a direction of gravity, of an arm of the user using the output of the acceleration sensor in the static posture; estimates a position of the neck or the shoulder of the user using the inclination and information of a length of the arm of the user; and calculates the third line, based on the estimate.

14. The calculation processing circuit as set forth in claim 11, wherein:
the second line extends in a direction crossing a ball-hitting surface of the sporting gear.

15. A motion analysis device, comprising:
a first calculation unit that uses an output of an inertial sensor that measures a swing of a sporting gear to: (i)

specify a first plane including (a) a first line that extends in an extending direction of a shaft portion of the sporting gear in a static state of the sporting gear; and (b) a second line showing a ball-hitting direction; and (ii) calculate an inclination, with respect to a direction of gravity, of a shaft portion of the sporting gear using the output from the inertial sensor in the static state;

a second calculation unit that uses the output of the inertial sensor to specify a second plane including: (a) a third line connecting a neck or a shoulder of a user of the sporting gear in a static posture of the user to a ball-hitting position; and (b) the second line showing the ball-hitting direction; and an output device that outputs an image of the first plane and the second plane calculated by the first calculation unit and the second calculation unit, so that a user of the sporting gear can view the image of the swing of the sporting gear, wherein:

the calculation unit uses the output of the inertial sensor to specify a second plane including: (a) a third line connecting a neck or a shoulder of a user of the sporting gear in a static posture of the user to a ball-hitting position; and (b) the second line showing the ball-hitting direction, the first plane is displayed separately from the second plane, and the image is used as an indication of good or bad ball hitting.

16. The motion analysis device as set forth in claim 15, wherein:

the inertial sensor is mounted to the shaft portion of the sporting gear.

17. The motion analysis device as set forth in claim 15, wherein:

image data of at least one of the first and second planes is generated.

18. The motion analysis device as set forth in claim 15, wherein:

a swing trajectory of the sporting gear is calculated, and (i) at least one of the first and second planes and (ii) the swing trajectory are displayed, the swing trajectory of the sporting gear being different between a back swing and a down swing of the sporting gear.

\* \* \* \* \*